United States Patent [19]

Richmond et al.

[11] 4,067,403
[45] Jan. 10, 1978

[54] WIRE DRIVER HANDPIECE

[75] Inventors: James W. Richmond, Comstock Township, Kalamazoo County; Russell K. Eaton, Kalamazoo Township, Kalamazoo County, both of Mich.

[73] Assignee: Stryker Corporation, Kalamazoo, Mich.

[21] Appl. No.: 713,921

[22] Filed: Aug. 12, 1976

[51] Int. Cl.² .................................... H01B 17/16
[52] U.S. Cl. ............................ 173/163; 279/30; 279/75; 24/136 A
[58] Field of Search ............. 173/163; 279/30, 75; 24/136 A, 115 R, 244, 263 SW; 403/325, 327

[56] References Cited

U.S. PATENT DOCUMENTS

| 1,026,567 | 5/1912 | Delihanty | 279/30 |
| 1,056,076 | 3/1913 | Wiard | 279/75 |
| 2,959,422 | 11/1960 | Manos | 279/30 |
| 3,398,965 | 8/1968 | Cox | 279/75 |
| 3,674,281 | 7/1972 | Hedrick | 279/30 |
| 3,718,340 | 2/1973 | Stewart | 173/163 |
| 3,975,032 | 8/1976 | Bent et al. | 279/75 |

Primary Examiner—Robert A. Hafer
Attorney, Agent, or Firm—Blanchard, Flynn, Thiel, Boutell & Tanis

[57] ABSTRACT

Chuck for a gear reduction surgical rotary driver. There is provided for a controlled speed surgical driver an automatically releasable chuck for grasping tools of a very small diameter such as the wire used in bone pinning. In a driver having a conventional high-speed drive motor and speed reduction means, there is provided a frustro conical ramp, of generally circular cross section, and diverging outwardly toward the working end of the tool. A wire carrier is arranged for longitudinal sliding movement in the end of said tool and having a portion thereof projecting beyond said tool. Said wire carrier receives the wire centrally therethrough and carries three gripping devices which act between the wire and said ramp. Two of said gripping devices are preferably of ball shape and the third thereof is of generally disk shape with a rounded periphery whereby to project between said balls and engage a wire or other tool of small diameter. Resilient means push said carrier against said ramp and same is manually retractable therefrom. Thus, by manually retracting the carrier, the wire may be inserted, will be normally held firmly in place by said balls and disk and may be again removed by manually retracting said carrier against said resilient means.

3 Claims, 5 Drawing Figures

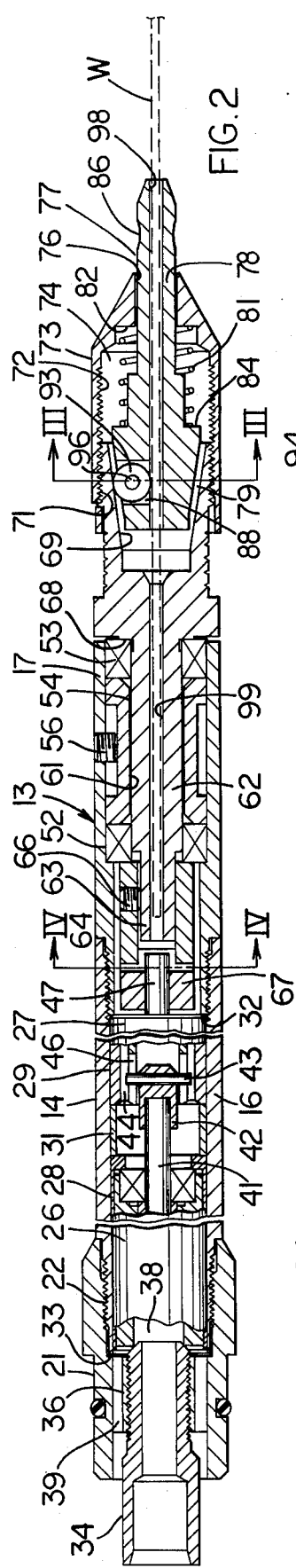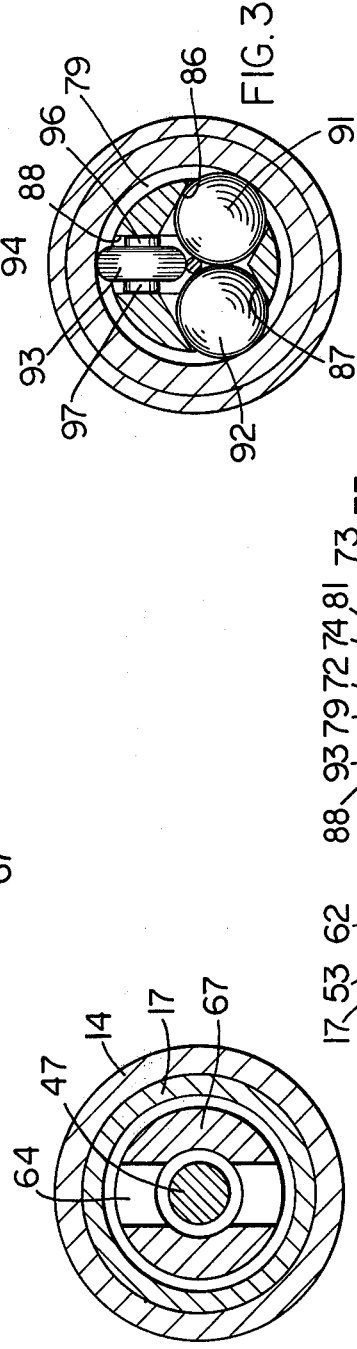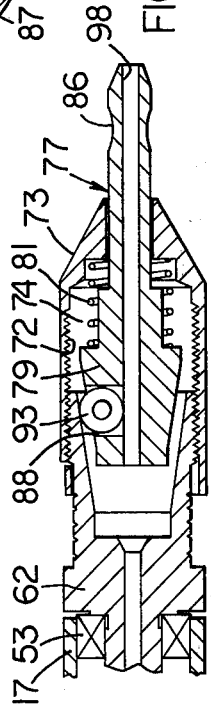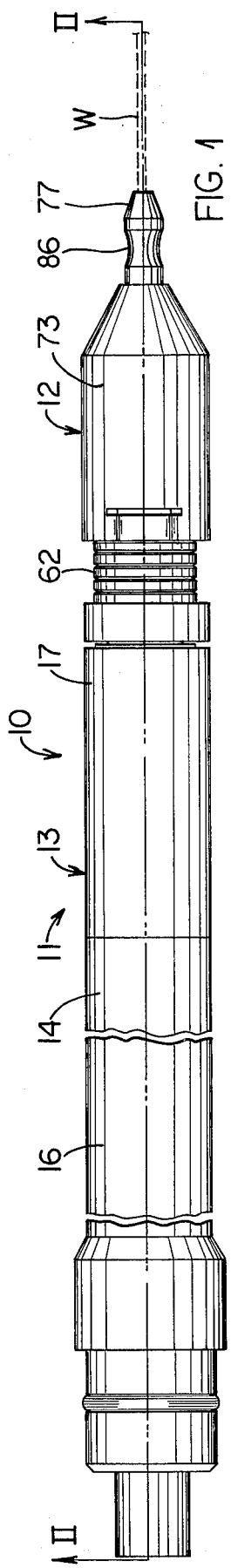

WIRE DRIVER HANDPIECE

FIELD OF THE INVENTION

The invention relates to chuck means for use with a gear reduction surgical driver and particularly one adapted for holding a tool of very small diameter, such as the wire normally used for pinning bones in orthopedic surgery.

BACKGROUND OF THE INVENTION

In orthopedic surgery, it is common to insert lengths of wire into bones for pinning same into a desired position and to hold same in predetermined relationship to each other. In so doing, it becomes necessary to drive the wire through the bones. Thus, the driver also becomes the wire dispenser and the surgeon is required to have at hand only a single tool.

Further, if the tool is to be used as a wire dispenser, it is necessary that same hold a reasonable length of wire, hold same firmly and rigidly while the tool is functioning as a driver but be capable by simple manipulation of enabling the wire to be withdrawn as desired as same is used.

It is well known in conventional chuck construction for drills and similar machine tools that chucks for tools of very small diameter present difficulty in insuring adequate engagement of such tools. Thus, conventional chucks of this type, usually collet chucks, normally require separate manipulation, often with a key device, for tightening and loosening the tool held thereby. Such separate manipulation of the chuck under the usual surgical conditions presents extreme inconvenience at best at it is highly desirable that a chuck be provided which will effectively hold a tool such as a wire of very small diameter and yet which can be readily engaged and disengaged by simple manual manipulation and without the need for a separate tool.

Accordingly, the objects of the invention include:

1. To provide a chuck adaptable for use with a gear reduction surgical driver for holding a rotatable tool of very small diameter.

2. To provide a chuck, as aforesaid, which for a given wire size will require no adjustment thereof for insertion of a tool or during operation thereof and the tool can be released in a simple manner for removal.

3. To provide a chuck, as aforesaid, which will be automatically engaged by constantly acting resilient means but can be released by a simple manual manipulation.

4. To provide a chuck, as aforesaid, wherein the release thereof can be accomplished without the use of a separate tool.

5. To provide a chuck, as aforesaid, whose parts are simple and hence will be capable of long and rigorous use with a minimum of maintenance.

6. To provide a chuck, as aforesaid, which will be completely reliable in operation, whose gripping will be automatic and which will automatically compensate for any wear experienced by the parts.

Other objects and purposes of the invention will be apparent to persons acquainted with apparatus of this general type upon reading the following disclosure and inspection of the accompanying drawings.

BRIEF DESCRIPTION OF THE DRAWINGS

In the drawings:

FIG. 1 is an elevational view, partially broken, of the driver embodying the chuck of the invention.

FIG. 2 is a longitudinal section of said driver taken on the line II—II of FIG. 1.

FIG. 3 is a sectional view taken on the line III—III of FIG. 2.

FIG. 4 is a sectional view taken on line IV—IV of FIG. 2.

FIG. 5 is a view corresponding to the rightward end of FIG. 2 showing the chuck in an alternate position.

SUMMARY OF THE INVENTION

Briefly summarizing the invention, there is provided a manually manipulatable driving structure having a conventional motor and speed changing mechanism for rotatively driving the chuck. Said chuck comprises structure defining an internally facing plurality of three circumferentially spaced ramps (or in the illustrated embodiment a single frustro conical ramp means of circular cross section) diverging outwardly toward the working end of the chuck. A tool carrier is mounted for axially slidable movement toward and away from said ramps and resilient means are provided for normally urging same toward said ramps. A central opening is provided through said tool carrier for reception of the tool, as a wire, and openings are provided in said tool carrier for the reception of multiple gripping members which are carried in said openings and bear externally against said ramps and internally against a tool within said tool carrying opening. In the illustrated embodiment, there are three gripping members, two of which are balls and the third thereof is a disk of rounded periphery for extending between said balls and engaging a tool, as a wire, of very small diameter. A typical diameter for which the tool in the illustrated embodiment is designed is about 1/16 inch or less in diameter.

DETAILED DESCRIPTION

Much of the driver's structure herein dealt with is substantially similar to that shown in U.S. Pat. to Barnett, No. 3,734,652 (assigned to the same assignee as the present application) and also similar to the presently pending application of Richmond and Rhodes, Ser. No. 688 567 (also assigned to the same assignee as the present application) and reference to both said patent and said application is herein made for details thereof. However, for convenience in assuring a full understanding of the present invention, a brief description of said driver structure will follow herein as an example of one typical driver unit with which the chuck of the invention may be utilized. It will be understood, however, that such description of said driver mechanism is illustrative only and that insofar as the chuck of the invention is concerned, it may be driven by any source of rotative power convenient or appropriate to a given use.

DETAILED DESCRIPTION

FIG. 1 illustrates a hand-held surgical instrument 10 which includes a handpiece assembly 11 to which is attached a chuck assembly 12.

The handpiece assembly 11 includes a handpiece 13 which is formed primarily by a housing member 14 having a straight tubular grip portion 16 of substantial length and a short tubular nose part 17 integrally connected to the forward end of the grip portion.

A cartridge-type motor 26 of any conventional type is removably positioned within the grip portion 16, which motor may, if desired, be connected in series with a cartridge-type speed reducer 27, which is also removably positioned within the grip portion 16. These cartridges 26 and 27 have outer sleevelike housings 28 and 29, respectively, so that the individual cartridges can each be slidably inserted into and removed from the rearward end of the grip portion 16. Both the motor and speed reducer cartridges are entirely selfcontained so that each can be handled as a single unit. The motor cartridge 26 contains therein a suitable motor, preferably a conventional pneumatic motor, so as to permit the desired speed of rotation of the surgical tool. The specific configuration of the speed reducer disposed within the cartidge 27 can also be of conventional, such as a gear-type speed reducer, so as to achieve the desired speed ratio between the input and output ends thereof.

The forward end of the speed reducer cartridge 27 is adapted to abut against a shoulder 32 formed internally of the grip portion 16 for defining the innermost position of the cartridge. A spacer sleeve 31 is slidably received within the grip portion 16 and disposed between the housings of the cartridges 26 and 27 for maintaining same in the desired axially spaced relationship. The rearward end of the motor cartridge in turn abuts against an internal annular shoulder 33 formed on the adapter sleeve 21, whereby the cartridges 26 and 27 are stationary confined with a housing 14.

To supply pressure fluid, namely air (assuming the motor to be an air motor), to the motor cartridge 26, there is provided an intake tube 34 fixedly disposed concentrically within the adapter sleeve 21 as by means of a threaded connection 36 therebetween. The inner end of intake tube 34 is disposed in bearing engagement with the adjacent rearward end of the motor cartridge 26 so that the air supply passage through the tube 34 is thus in continuous communication with the inlet passage 38 formed in the motor cartridge 26. To permit discharge of air from the motor, there is provided a plurality of small discharge passages 39 formed in the adapter sleeve 21 and opening axially through the rearward end thereof so that the air is discharged thereby into and through a passageway which surrounds the intake tube 34. The adapter sleeve 21 and intake tube 34 are conventionally connected to an elongated flexible conduit assembly (not shown) having concentric inner and outer flexible tubes so that the pressurized supply air can be supplied through the inner tube and the discharge air removed through the outer tube.

The cartridge motor unit 26 has an output shaft 41 projecting therefrom and provided with a cylindrical clutch portion 42 thereon, which clutch portion is adapted to be received within, and clutched to, the rearward end of the input shaft 44 of the speed reducer unit 27. Such clutching may be of any convenient type, such as by the drive pin and slot arrangement indicated at 43 and 46.

The speed reducer unit 27 has an output shaft 47 which is coaxially aligned with the input shaft 44 and carries thereon a collar member 67 further discussed hereinafter. A sleeve 54 is held in the nose part 17 by the set screw 56 and supports bearings 52 and 53 coaxially with shaft 47.

Extending through the central opening 61 of the sleeve 54, and supported on and by the bearings 52 and 53, is a shaft 62. The inner end of said shaft includes a projection 63, here of reduced diameter, which is encircled by a sleeve 64. Said sleeve 64 is held in place on and with respect to the projection 63 by any convenient means, such as a set screw 66, and is held between the end of the bearing 52 and the output collar 67. Said collar 67 is arranged to drive the sleeve 63 in any convenient manner, such as by a slotted portion of said collar receiving a projecting portion of said sleeve, whereby the output of the speed reducer 27 is conducted through the sleeve 64 to effect rotation of the shaft 62.

The forward, or rightward as appearing in FIG. 2, end of the shaft 62 is provided with a substantial shoulder 68 which bears against the bearing 53 for limiting movement of said shaft leftwardly, as appearing in FIG. 2. At the forward end of said shaft there is provided an opening 69 of truncated conical shape diverging forwardly toward and through the end of said shaft. The outer surface of the rightward end of said shaft is threaded at 71 and receives the internal threading 72 of a cap member 73. Said cap member has an internal opening 74 which is of reduced diameter near the rightward end thereof to provide a guide opening 76.

Received within said internal opening 74 is the tool carrier 77. Same has a projecting portion 78 of diameter for smoothly sliding through said guide opening 76 and an enlarged tapered head 79, the tapering of which conforms to the tapering of the internal opening 69. A spring 81 extends between a seat 82 in the cap member 73 and a seat 84 at the forward end of the head 79. Said spring 81 thus provides a constant force urging the tool carrier 77 leftwardly toward the surface 69 and, if desired, means such as the annular depression 86 may be provided at the end of the portion 78 to facilitate the manual grasping thereof to draw same rightwardly against the force of said spring.

Turning now to FIG. 3, there is provided in the head 79 a group of three slots 86, 87 and 88, same being arranged on central planes defining preferably equal angles with respect to each other. The slots 86 and 87 receive balls 91 and 92, respectively, and will normally be of somewhat greater width than the slot 88. Slot 88 receives a relatively narrow disk 93, same having a rounded perimeter 94 and being provided with hubs 96 and 97, said hubs functioning to hold said disk in proper alignment in and with respect to the sides of the slot 88. Said disk is of the same diameter as the balls but its rounded perimeter will be rounded on a smaller radius than that of said balls. If desired, of course, said hubs can be omitted and the slot 88 narrowed to a width only a clearance distance greater than the thickness of the disk 93 but the somewhat wider slot as shown is preferred in view of the difficulty of making a narrower slot in the small sizes involved.

All three of said slots are of axial length only sufficient to receive and permit rotation of the balls 91 and 92 and of the disk 93, respectively, the length of said slot 88 being illustrated in FIG. 2 and that of slots 86 and 87 for said balls being generally similar. Centrally within both the tool carrier 77 and the shaft 62 are coaxial openings 98 and 99 which receive the wire, or other tool, indicated by the broken line W. The dimensioning of the balls 91 and 92 and of the disk 93 as best illustrated in FIGS. 2 and 3 is such that when the tool carrier 77 is urged leftwardly by the spring 81, said disk and balls will bear against the surface 69 and be urged thereby into tight engagement with the wire W but upon movement of the tool carrier 77 forwardly, that is rightwardly as appearing in FIG. 2, said disk and balls are released and the tool is also released.

OPERATION

While the operation of the device has been somewhat indicated above, it will be reviewed fully to insure a complete understanding of the invention.

The motor 26 and a gear reducer 27, together with the parts immediately associated with each thereof, have already been indicated above as conventional, have been described in the literature to which reference has above been made, and hence need not be further reviewed here. It is sufficient to say that insofar as the present invention is concerned, the output collar 67 is caused by any convenient means to rotate at a preselected rotative speed by any convenient means desired. The collar then acts through the sleeve 64 and the set screw 66 to drive the shaft 62. With the tool carrier 77 urged leftwardly by the spring 81 to jam the clamp members, namely the disk 93 and balls 91 and 92, against the tool, here the wire W, rotation of the shaft 62 will act through said disk and balls to effect rotation of both the tool carrier 77 and the tool as desired. Thus, where the tool is a wire, same can be used as a drill in a presently known manner.

When the hole has been drilled into the bone, the wire is then clipped at a proper length with respect to the bone and the instrument removed. It is necessary then only to grasp the tool carrier 77 manually, as by the groove 86, pull same forwardly (rightwardly in FIG. 2) whereby to release the gripping of said wire by the clamp members, draw same outwardly the desired distance for the next manipulation thereof, then release the tool carrier 77. Same will respond to the spring 81 to move the clamp members again into gripping engagement between the surface 69 and the wire and the instrument is ready for the next use.

If a wire is to be withdrawn and changed, or if a substantially used wire is to be replaced, the same procedure is followed, namely manually withdrawing the tool carrier 77 forwardly to release the wire then in the device and inserting a new wire into place.

If no wire is in place it is obvious from inspection of FIG. 3 that the disk and balls will merely engage each other and no improper displacement of the parts will occur.

Although particular preferred embodiments of the invention have been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. In a surgical instrument for rotatably driving an elongated rodlike tool, such as a wire, comprising:
    a manually graspable hollow casing comprising a tool handle;
    a shaft rotatably supported within said casing and arranged to be rotatably drive about its axis by a source of rotative power, said shaft having an enlarged shaft portion positioned adjacent and projecting axially outwardly from the front end of said casing, said enlarged shaft portion having an axially elongated interior opening formed therein and extending divergingly through the forward end of said shaft portion, said opening being bounded by a frusto conical surface positioned at a small angle with respect to the axis of said shaft;
    a tool carrier positioned coaxially with and partially telescoped into said interior opening, said tool carrier having a central opening extending axially therethrough in substantially coaxial alignment with said shaft, said tool carrier also having three slots extending radially therethrough from said central opening to the exterior peripheral surface of said tool carrier, said three slots being circumferentially spaced apart and disposed with the radial center lines thereof within substantially a single plane which extends perpendicularly to said axis;
    three clamping members positioned respectively within said slots and adjacent said conical surface for responding to axial movement of said tool carrier along and with respect to said conical surface for effecting movement of said clamping members radially of said tool carrier, said clamping members entering at least partially into said central opening in at least one axial position of said tool carrier for clamping engagement with a rodlike tool positioned therein;
    two of said clamping members comprising identical balls and the third clamping member comprising a disk which is so related relative to its respective slot that the axis of said disk is spaced from but substantially perpendicular to the axis of said tool carrier, said disk and said balls all being of the same diameter, and said disk having a peripheral surface adapted for engagement with the tool which is of a rounded convex configuration in the axial direction of the disk;
    whereby upon rearward axial movement of said tool carrier into said interior opening, said clamping members will grip a tool positioned within said tool carrier and upon forward axial movement of said tool carrier, said clamping members will release said tool.

2. An instrument according to claim 1, wherein there is provided a sleevelike cap member arranged on and for rotation with the enlarged shaft portion, said cap member projecting axially forwardly from said shaft portion and having a hollow interior communicating with said interior opening, said tool carrier having an enlarged portion movably accommodated within said interior opening and the hollow interior of said cap member, said enlarged portion being positioned for cooperation with said conical surface and having said radial slots formed therein, said cap member having a front wall which is spaced axially from the enlarged portion of said tool carrier and is provided with a small guide opening extending therethrough in coaxial alignment with said shaft, said tool carrier including a reduced diameter elongated shaft part which is fixed to and projects coaxially forwardly from said enlarged portion, said shaft part extending axially slidably through said guide opening, the central opening as formed in said tool carrier extending through both said enlarged portion and said elongated shaft part, and spring means coacting between said cap member and said tool carrier for resiliently urging said tool carrier axially inwardly into said interior for normally maintaining said clamping members in a position for gripping engagement with a tool.

3. An instrument according to claim 1, wherein the rounded convex configuration of the peripheral surface on said disk is formed by a radius which is substantially less than the radius of said balls.

* * * * *